US00PP24465P3

(12) United States Plant Patent
Roe

(10) Patent No.: US PP24,465 P3
(45) Date of Patent: May 20, 2014

(54) ***CITRUS RETICULATA* PLANT NAMED 'WG3'**

(50) Latin Name: *Citrus reticulata*
Varietal Denomination: WG3

(75) Inventor: Bill Roe, Eagle Lake, FL (US)

(73) Assignee: GJH LLC, Winter Haven, FL (US)

( * ) Notice: Subject to any disclaimer, the term of this patent is extended or adjusted under 35 U.S.C. 154(b) by 113 days.

(21) Appl. No.: 13/385,097

(22) Filed: Jan. 31, 2012

(65) Prior Publication Data

US 2013/0198917 P1 Aug. 1, 2013

(51) Int. Cl.
*A01H 5/00* (2006.01)

(52) U.S. Cl.
USPC ..... Plt./201; Plt./202

(58) Field of Classification Search
USPC ..... Plt./201, 202
See application file for complete search history.

*Primary Examiner* — June Hwu
(74) *Attorney, Agent, or Firm* — Cassandra Brigh

(57) ABSTRACT

A new and distinct *Citrus reticulata* cultivar named 'WG3' is disclosed, characterized by having distinctive fruit that peels easily and dry and can be eaten with little mess. It also has very low seed average of less than 2 seeds per fruit. Additionally, the new variety produces fruit that does not pull very much when ripe until overripe and maintains acid during ripening.

2 Drawing Sheets

Latin name of the genus and species: *Citrus reticulata*.
Variety denomination: 'WG3'.

BACKGROUND OF THE INVENTION

The new cultivar is a product of a planned crossing program in 2001 under the direction of the inventor, Bill Roe, a citizen of The United States. The parents are unnamed proprietary seedlings of *Citrus reticulata*.

This new variety was found in November 2006 in a commercial nursery in Winter Haven, Fla. Plants were first propagated by tissue culture in 2006 and subsequently grafted onto rootstocks US-897 and US-942. Development, evaluation, tissue culture and grafting all first took place at the inventor's commercial nursery in Winter Haven, Fla. USA. Subsequent evaluations of the variety have shown the characteristics to be true to type.

SUMMARY OF THE INVENTION

The cultivar 'WG3' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'WG3' These characteristics in combination distinguish 'WG3' as a new and distinct *Citrus reticulata* cultivar:

1. Peel is removed easily.
2. Very low seed production, average less than 2 per fruit.
3. Peel does not pull away from fruit significantly until overripe.
4. Acidity maintained during ripening.
5. Can be peeled and eaten without a mess.
6. Peel is dry.
7. Very little albedo.

COMPARISON TO PARENTS

Plants of the new cultivar 'WG3' are similar to plants of the seed parent in most horticultural characteristics, however, plants of the new cultivar 'WG3' produce fruit with significantly less seeds. Compared to the pollen parent, 'WG3' produces firmer fruit. Fruit of 'WG3' has less acid than the pollen parent and when peeled, is overall cleaner.

COMMERCIAL COMPARISON

The new variety is best compared to the commercial variety, 'Dancy,' unpatented. 'WG3' is similar to 'Dancy' in many horticultural characteristics, however, 'WG3' produces fruit with significantly less seeds, of more uniformed color as well as firmer. Additionally, fruit of the new variety 'WG3' are distinctively less susceptible to fungi and its peel pulls away from the fruit less than 'Dancy'.

'WG3' can also be compared to 'Sunburst', unpatented. The two varieties are similar in many horticultural characteristics, however 'WG3' produces fruit that is not as deep orange in external color and possesses a smoother peel that peels easier and cleaner, with less albedo. Compared to 'Sunburst', 'WG3' possesses fruit that has much lower seed count, and matures slightly later.

BRIEF DESCRIPTION OF THE PHOTOGRAPH

Figure 1:
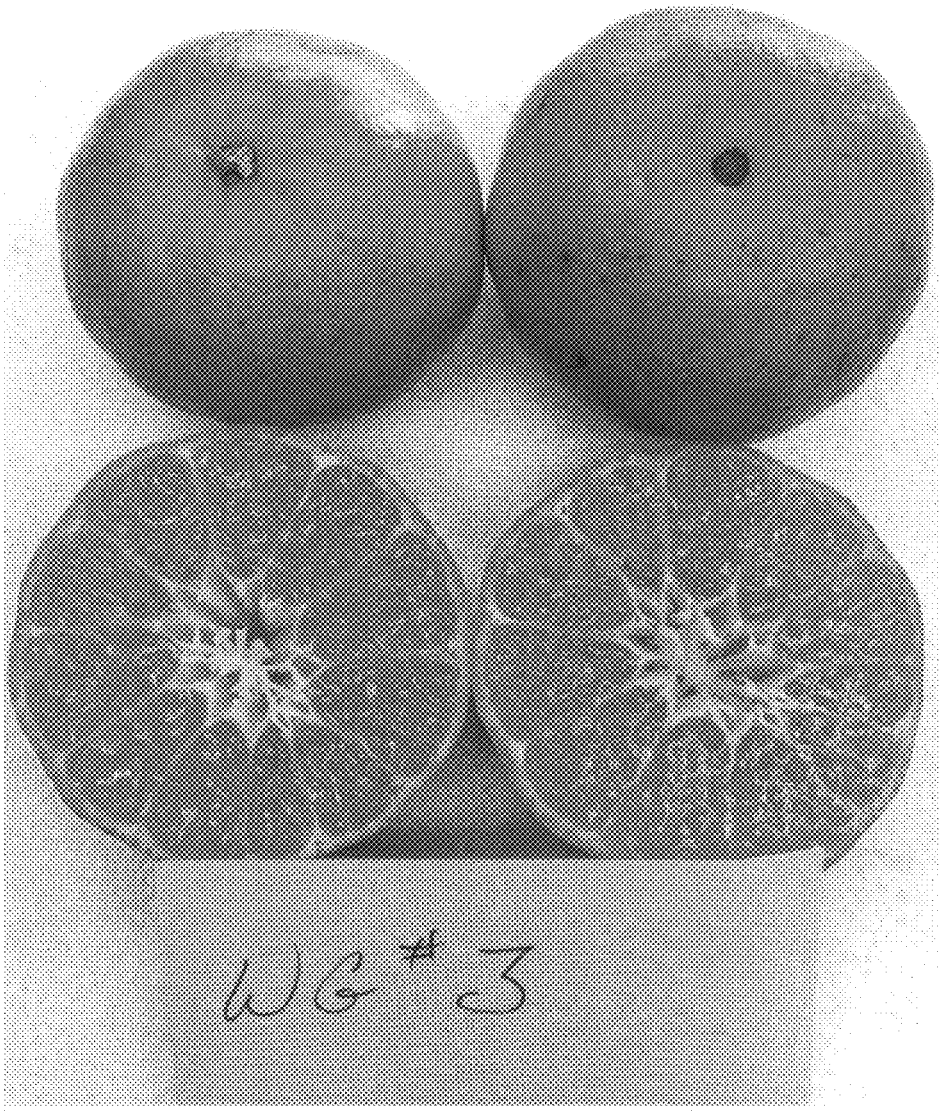

The accompanying photograph in FIG. 1 illustrates in full color examples of typical fruit harvested from 'WG3'.

Figure 2:
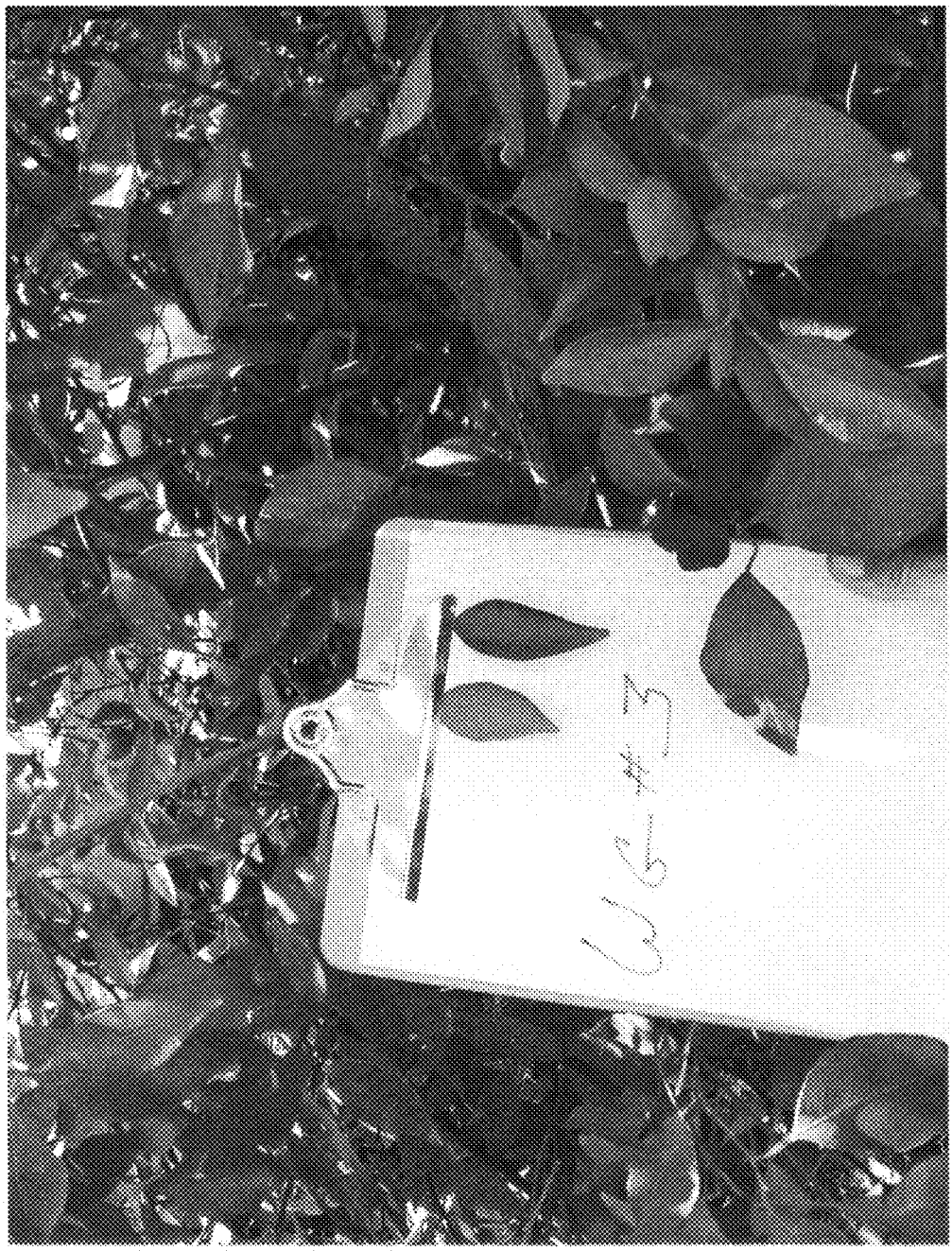

FIG. 2 illustrates in full color typical foliage of 'WG3'.

Photographs are taken of plants approximately 3 years old. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'WG3' plants grown outdoors under commercial trial conditions in Winter Haven, Fla. USA. The growing temperature ranged from 4° C. to 37° C. during the day and −5° C. to 22° C. at night Botanical classification: *Citrus reticulata* 'WG3'.

PROPAGATION

'WG3' is typically grafted onto rootstock of 'Swingle'. US 897 and US 942

PLANT

Age of the plant described: Approximately 3 years.
Height: 230 cm.
Growth rate: Approximately 3 years to 200 cm.
Plant spread: Generally an overall narrow tree, fruit tends to grow inside or on heavy limbs that weep down under heavy cropset. Individual shoots grow 60-90 cm. but then hang down heavily under fruit loading.
Vigor: Good with heavy Spring flush and fruit-set with cross-pollination.
Length of primary lateral branches: Approximately 45-60 cm.
Branch diameter: Average 2.5-3.5 cm.
Quantity of lateral branches: 6-7.
Angle of lateral branches from main trunk: 135-150 degrees.
Branching arrangement: Profuse secondary branching after 45-60 cm. of straight growth.
Trunk texture: Smooth.
Trunk diameter: Average 6.5-7.5 cm on a 3 year old plant.

FOLIAGE

Leaf:
- *Average length*.—Range of 5.5-11.0 cm. Average of 8-9 cm.
- *Average width*.—Range of 2.5-6.0 cm. Average of 4 cm.
- *Arrangement*.—Alternate.
- *Shape of blade*.—Ovate.
- *Apex*.—Acute.
- *Base*.—Attenuate.
- *Attachment*.—Stalked.
- *Margin*.—Smooth with slight dentations.
- *Texture of top surface*.—Smooth.
- *Texture of under side*.—Slightly rough with pronounced center vein.
- *Color*.—Mature foliage upper side: Near RHS Green 139A. Mature foliage under side: Near RHS Green 141B.
- *Petiole*.—Length: Average length 1-1.5 cm. Pubescence: None. Color: Near RHS Green 143C.

FLOWER

Inflorescence and flower type and habit: Single rotate flowers emerging from leaf axils.
Flower longevity on plant: Approximately 2 weeks.
Persistent or self-cleaning: Self-cleaning.
Bud:
- *Shape*.—Elongated, irregular sphere.
- *Length*.—Average 2.9 cm.
- *Diameter*.—1.6 cm.
- *Color*.—Near RHS White 155A.

Flower size:
- *Diameter*.—Average 3.9 cm.
- *Depth*.—Average 3.2 cm.

Corolla/petals:
- *Arrangement*.—Rotate.
- *Petal quantity*.—5.
- *Length*.—Average 2.0 cm.
- *Width*.—Average 1.1 cm.
- *Texture*.—Glabrous.
- *Apex*.—Acute.
- *Base*.—Blunt.
- *Shape*.—Oblong.
- *Margin*.—Entire.
- *Aspect*.—Flat.
- *Color*.—When opening: Upper surface: Near RHS White 155D. Lower surface: Near RHS White 155D. Fully opened: Upper surface: Near RHS White 155D. Lower surface: Near RHS White 155D.

Calyx/sepals:
- *Quantity per flower*.—5.
- *Shape*.—Linear, partially fused at base.
- *Length*.—Average 1.5 cm.
- *Width*.—0.4 cm.
- *Apex*.—Acute.
- *Base*.—Fused.
- *Margin*.—Entire.
- *Texture*.—Glabrous.
- *Color*.—Upper Surface: Near RHS Green 137B. Lower Surface: Near RHS Green 137B.

Pedicel:
- *Length*.—Average 2.5 cm.
- *Diameter*.—Average 0.25 cm.
- *Color*.—Near RHS Green 137A.
- *Orientation*.—Approximately 45 degree angle from leaf axil.
- *Texture*.—Glabrous.

Fragrance: Sweet, typical *Citrus* flower scent.

REPRODUCTIVE ORGANS

Stamens:
- *Number*.—Most commonly 15.
- *Filament length*.—Approximately 2.6 cm.

Anthers:
- *Shape*.—Globular.
- *Length*.—Approximately 0.3 cm.
- *Color*.—Near RHS Greyed-Orange 161D.
- *Pollen*.—Color: Near RHS Greyed-Orange 162A. Quantity: Moderate.

Pistil:
- *Number*.—1.
- *Length*.—Approximately 0.9 cm.
- *Style*.—Length: 0.8 cm. Color: Near RHS Green-Yellow 1D.
- *Stigma*.—Shape: linear. Color: Near RHS Green-Yellow 1B. Ovary Color: RHS Green 143B.

FRUIT

Color exocarp: Near RHS Orange-Red 30B.
Color mesocarp: Near RHS Orange 24D.
Flesh color: Near RHS Orange 28A.
Brix at consumption: 11.45.
Brix at harvest: 11.45. Acid of 1.05 Ratio of 10.90.
Average weight: 125 grams.
Minimum weight: 60 grams.
Maximum weight: 155 grams.
Height: Avg. 5 cm.
Width: Avg. 6.5-7 cm.
Segment number per fruit: A range averaging 8 to 12.
Segment size:
- *Average width*.—1.4 cm.
- *Average length*.—3.9 cm.

Fruit peduncle length: Range between 60-130 mm. Average of 65 mm.

Fruit peduncle width: Range between 50-70 mm. Average of 60 mm.

General shape: Oblate.

Fruit aroma: Tart, sweet.

Skin color at harvest: Near RHS Orange 28B or Orange 28A.

Skin/rind thickness: Thin: 2 mm.

Skin adherence to flesh at maturity: Releases clean and dry.

Skin/rind texture: Mostly smooth. Oil cells are visible, but peel is not pebbly.

Base: Not necked, but not completely flat.

Other fruit features: Fruit with pronounced oil cells yet fairly slick peel. Fruit peels very dry and very easily with little or no albedo. Flavor is delightful and carries acid through ripening period. Skin uniquely does not pull and holds shape, variety is somewhat unique in that characteristic.

Shipping quality: The inventor measures shipping quality with two categories: Perishability; Damage caused by clear rot, blue-green mold and stem end rot. Misshapen fruit; Damage to the fruit shape when packed in a commercial 35 to 40 pound shipping box. 'WG3' produces a moderately firm fruit, with a somewhat tightly clinging peel. The internal characteristic of the fruit is soft. Fruits of 'WG3' are not well suited for shipping in commercial shipping boxes. Fruits are packed and shipped in consumer packing, which consists of small 5 pound packages, or self-supporting boxes.

Harvest time:

*First harvest*.—About November 10.

*Last harvest*.—About January 10-15.

Overall cropping quantity: Fruits heavily with cross pollination but grows almost no seeds.

Mature seed color: Near RHS Yellow-White 158D.

Quantity seed per fruit: Less than 2. Non-viable.

Seed shape: Flat and misshapen.

Seed length: 12.5 mm.

Seed width: 5 mm.

OTHER CHARACTERISTICS

Storage life: Storage life is a minimum of 21 days at 2° C.

Disease/pest resistance: Neither resistance nor susceptibility to pathogens and pests common to *Citrus reticulata* have been observed.

Temperature tolerance: Tolerates low temperatures to approximately −5° C. without negative effects, tolerates high temperatures to approximately 37° C. without negative effects.

What is claimed is:

1. A new and distinct cultivar of *Citrus reticulata* plant named 'WG3' as herein illustrated and described.

* * * * *